(12) United States Patent
Vunjak-Novakovic et al.

(10) Patent No.: US 10,889,789 B2
(45) Date of Patent: Jan. 12, 2021

(54) PERFUSION BIOREACTOR WITH TISSUE FLOW CONTROL AND LIVE IMAGING COMPATIBILITY

(71) Applicant: The Trustees of Columbia University in the City of New York, New York, NY (US)

(72) Inventors: Gordana Vunjak-Novakovic, New York, NY (US); Sarindr Bhumiratana, Brooklyn, NY (US); Keith Yeager, Jersey City, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 16/373,516

(22) Filed: Apr. 2, 2019

(65) Prior Publication Data
US 2019/0225925 A1   Jul. 25, 2019

Related U.S. Application Data

(63) Continuation of application No. 14/782,630, filed on Oct. 6, 2015, now Pat. No. 10,301,584, which is a continuation of application No. PCT/US2014/034559, filed on Apr. 17, 2014.

(60) Provisional application No. 61/857,490, filed on Jul. 23, 2013, provisional application No. 61/813,378, filed on Apr. 18, 2013.

(51) Int. Cl.
| | | |
|---|---|---|
| C12M 1/00 | (2006.01) | |
| C12M 1/12 | (2006.01) | |
| C12M 3/00 | (2006.01) | |

(52) U.S. Cl.
CPC ............ *C12M 21/08* (2013.01); *C12M 23/40* (2013.01); *C12M 25/14* (2013.01); *C12M 29/10* (2013.01)

(58) Field of Classification Search
CPC ...... C12M 21/08; C12M 23/34; C12M 23/08; C12M 21/04; C12M 25/14; C12M 29/10; C12M 23/40
USPC .......... 435/294.1, 289.1, 297.2, 283.1, 297.1
See application file for complete search history.

(56) References Cited

U.S. PATENT DOCUMENTS

| | | |
|---|---|---|
| 5,416,022 A | 5/1995 | Amiot |
| 6,008,049 A | 12/1999 | Naughton et al. |
| 2002/0110905 A1 | 8/2002 | Barbera-Guillem et al. |
| 2009/0111180 A1 | 4/2009 | Vilendrer et al. |
| 2009/0233361 A1 | 9/2009 | Farhat et al. |
| 2011/0136225 A1 | 6/2011 | Vunjak-Novakovic et al. |
| 2012/0035742 A1* | 2/2012 | Vunjak-Novakovic ...... A61F 2/28 623/23.61 |

FOREIGN PATENT DOCUMENTS

| | | |
|---|---|---|
| WO | 2010102059 | 9/2010 |
| WO | 2010139337 | 12/2010 |

OTHER PUBLICATIONS

Australian Examination Report 1 mailed for application No. 2014253850, dated May 10, 2018, 3 pages.
(Continued)

*Primary Examiner* — Liban M Hassan

(57) ABSTRACT

A perfusion bioreactor chamber for engineering a broad spectrum of tissues. The bioreactor allows controlled distribution of fluid through or around scaffolding materials of various shapes, structures and topologies during prolonged periods of cultivation.

12 Claims, 14 Drawing Sheets

(56) References Cited

OTHER PUBLICATIONS

Bhumiratana, "Controlling Tissue Matrix Assembly of Human Mesenchymal Stem Cells toward Engineering Native-like Bone, Cartilage, and Osteochondral Grafts", Submitted in partial fulfillment of the Requirements for the degree of Doctor of Philosophy in the Graduate School of Arts and Sciences, Jan. 1, 2012, 117—121 page.
EPO, Extended European search Report mailed for EP application No. 14784780.0, dated Nov. 14, 2016, 5 pages.
JPO, Notice of Decision to Grant mailed for JP application No. 2016509109, dated Nov. 6, 2018, 5 pages.
USPTO, Final Office Action mailed for U.S. Appl. No. 14/782,630, dated Aug. 18, 2017, 18 pages.
USPTO, Notice of Allowance mailed for U.S. Appl. No. 14/782,630, dated Jan. 11, 2019, 13 pages.
USPTO, Non-Final Office Action dated for U.S. Appl. No. 14/782,630, dated Jan. 25, 2017, 15 pages.
USPTO, Non-Final Office Action mailed for U.S. Appl. No. 14/782,630, dated Jul. 12, 2018, 8 pages.
USPTO, Non-Final Office Action mailed for U.S. Appl. No. 14/782,630, dated Jun. 8, 2016, 11 pages.
WIPO, International Preliminary Report on Patentability mailed for PCT application No. PCT/US2014/034559, dated Oct. 20, 2015, 5 pages.
WIPO, International Search Report and Written Opinion mailed for PCT application No. PCT/US2014/034559, dated Sep. 23, 2014, 6 pages.
Grayson, et al., "Engineering anatomically shaped human bone grafts", PNAS, Feb. 23, 2010, vol. 107, No. 8, pp. 3299-3304.
JPO, "Office Action mailed in Japanese Application No. 2018-229138", dated Nov. 13, 2019, 5 Pages.
Canada Patent Office, Office Action mailed for U.S. Pat. No. 2,909,187, dated Feb. 13, 2020, 3 pages.
Korean Office Action in Korean Application No. 10-2015-7032861 dated Oct. 16, 2020, 17 pages.

* cited by examiner

PERFUSION BIOREACTOR WITH TISSUE FLOW CONTROL AND LIVE IMAGING COMPATIBILITY

RELATED APPLICATIONS

This application is a continuation of, and claims priority to, U.S. patent application Ser. No. 14/782,630, filed Oct. 6, 2015, which is a continuation under 35 U.S.C. § 371 of International Application No. PCT/US2014/034559 filed Apr. 17, 2014, which claims the benefit of U.S. Provisional Application No. 61/813,378, filed Apr. 18, 2013 and claims the benefit of U.S. Provisional Application No. 61/857,490, filed Jul. 23, 2013, the contents of which are incorporated herein by reference in their entirety.

STATEMENT REGARDING FEDERALLY SPONSORED RESEARCH

This invention was made with U.S. Government support under Grant No. NYCPF CU11-1915. The U.S. Government has certain rights in this invention.

BACKGROUND OF THE DISCLOSED SUBJECT MATTER

Field of the Disclosed Subject Matter

The disclosed subject matter relates to a system and apparatus for tissue engineering and harvesting. Particularly, the present disclosed subject matter is directed toward utilization of perfusion bioreactor chamber for engineering a broad spectrum of tissues that allows controlled distribution of fluid through or around scaffolding materials of various shapes, structures and topologies during prolonged periods of cultivation.

In the tissue engineering field, the present disclosure greatly simplifies and improves the techniques to optimize the properties of complex-shaped, multi-phase tissues for implantation and scientific research, as well as enable more insight into the tissue growth without interrupting culture.

BRIEF SUMMARY

According to an aspect of the present disclosure, a bioreactor culture chamber is provided. The bioreactor culture chamber includes a scaffold, at least one PDMS block, a plurality of manifolds, and a plurality of fluid routing blocks. The fluid routing blocks are configure with fluid routing structural features. The fluid routing blocks are configured to be nested within the manifolds. The bioreactor culture chamber also includes a case. The case is disposed exterior of the scaffold, PDMS block and plurality of manifolds.

According to another aspect of the present disclosure, a bioreactor culture chamber is provided. The bioreactor culture chamber includes a block. The block has at least one side, an approximately central cavity. The block has a plurality of channels extending from the at least one side to the approximately central cavity. The bioreactor culture chamber includes a fluid routing manifold. The fluid routing manifold includes an inlet and an outlet. The fluid routing manifold is in fluid communication with the plurality of channels. The bioreactor culture chamber includes an enclosure disposed about an exterior of the fluid routing manifold.

In some embodiments, the enclosure is substantially tubular. In some embodiments, the block comprises PDMS. In some embodiments, the enclosure exerts a compressive force on the fluid routing manifold. In some embodiments, the plurality of channels is configured such that each of the plurality of channels has substantially the same flow path resistance. In some embodiments, the bioreactor culture chamber includes a scaffold disposed within the approximately central cavity. In some embodiments, the scaffold comprises a plurality of cells. In some embodiments, the inlet is in fluid communication with a reservoir. In some embodiments, the reservoir comprises a nutrient solution. In some embodiments, the block and the enclosure are substantially transparent to x-rays. In some embodiments, the block and the enclosure are substantially transparent to MRI. In some embodiments, bioreactor culture chamber includes an additional fluid routing manifold having an inlet and an outlet. In such embodiments, the enclosure is disposed about an exterior of the additional fluid routing manifold. In some embodiments, the scaffold and the approximately central cavity are substantially the same shape.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

DETAILED DESCRIPTION OF EXEMPLARY EMBODIMENTS

Reference will now be made in detail to exemplary embodiments of the disclosed subject matter, an example of which is illustrated in the accompanying drawings. The apparatus and corresponding method of the disclosed subject matter will be described in conjunction with the detailed description of the system.

The methods and systems presented herein may be used for the design and utilization of a perfusion bioreactor chamber for engineering a broad spectrum of tissues that allows controlled distribution of fluid through or around scaffolding materials of various shapes, structures and topologies during prolonged periods of cultivation. The bioreactor disclosed herein also allows for use of two or more different culture media (e.g., to support the formation of composite tissues), control of oxygen concentration inside the tissue, and live imaging (e.g., by µCT, MRI) without interruption of culture.

Figure 1:
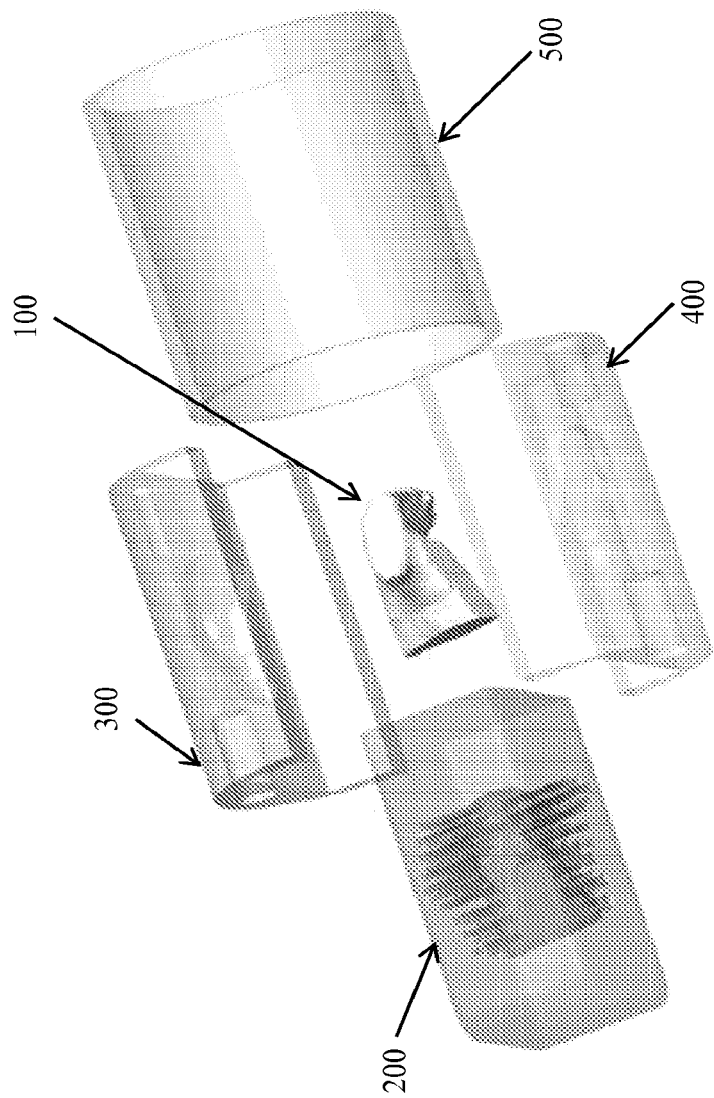
FIG. 1 is a schematic representation of an exploded-view of the components of the bioreactor culture chamber in accordance with the disclosed subject matter.
Figure 2:
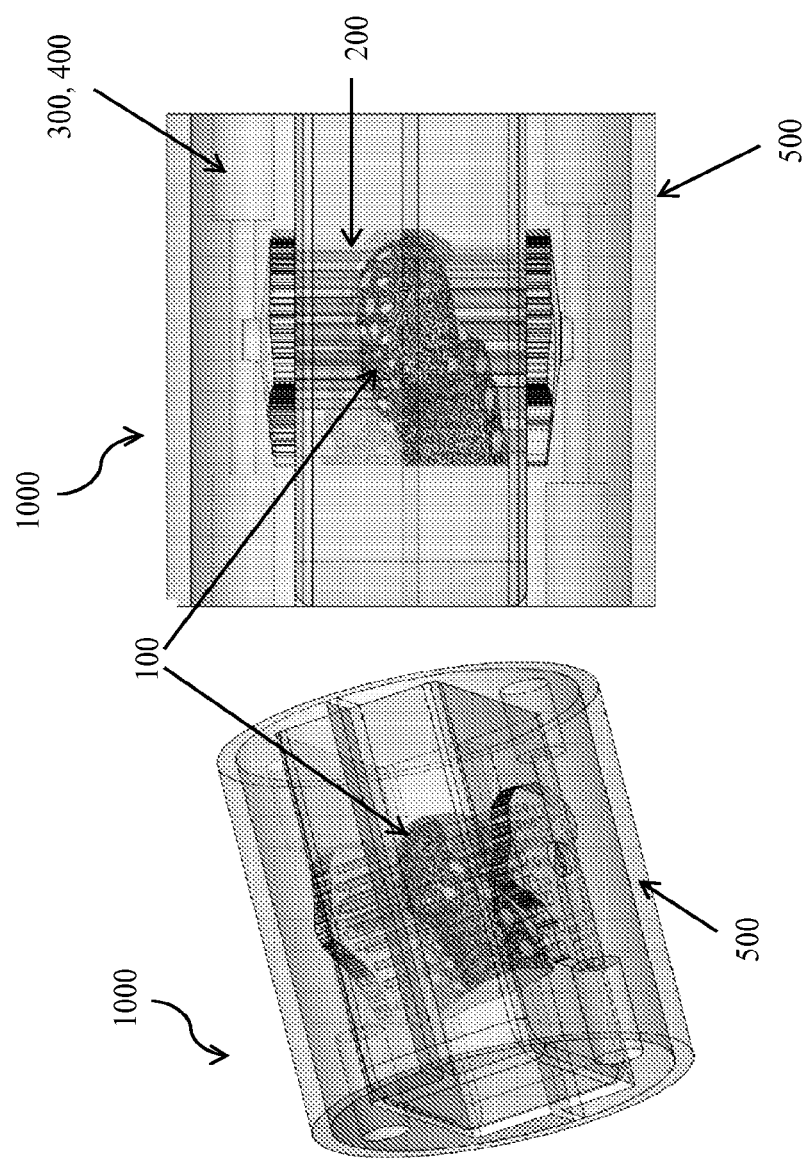
FIG. 2 is a schematic representation of the assembled bioreactor culture chamber of FIG. 1.

An exemplary embodiment of the bioreactor culture chamber is illustrated in FIG. 1 and includes five main components. These components include: a complex scaffold 100, a Polydimethylsiloxane (PDMS) block 200, two fluid-routing manifolds 300, 400, and a case 500. To assemble the bioreactor, the scaffold 100 is inserted into the PDMS block 200, which is specifically fabricated to match the construct shape. The PDMS block 200 is sandwiched between two fluid-routing manifolds 300, 400, while a tubular enclosure 500 slides over the assembly, providing a compressive force to tightly seal all the individual components together (as shown in FIG. 2) as an assembled unit 1000. The fluid-routing manifolds 300, 400 are designed with a plurality of ports for medium perfusion.

Figure 3:
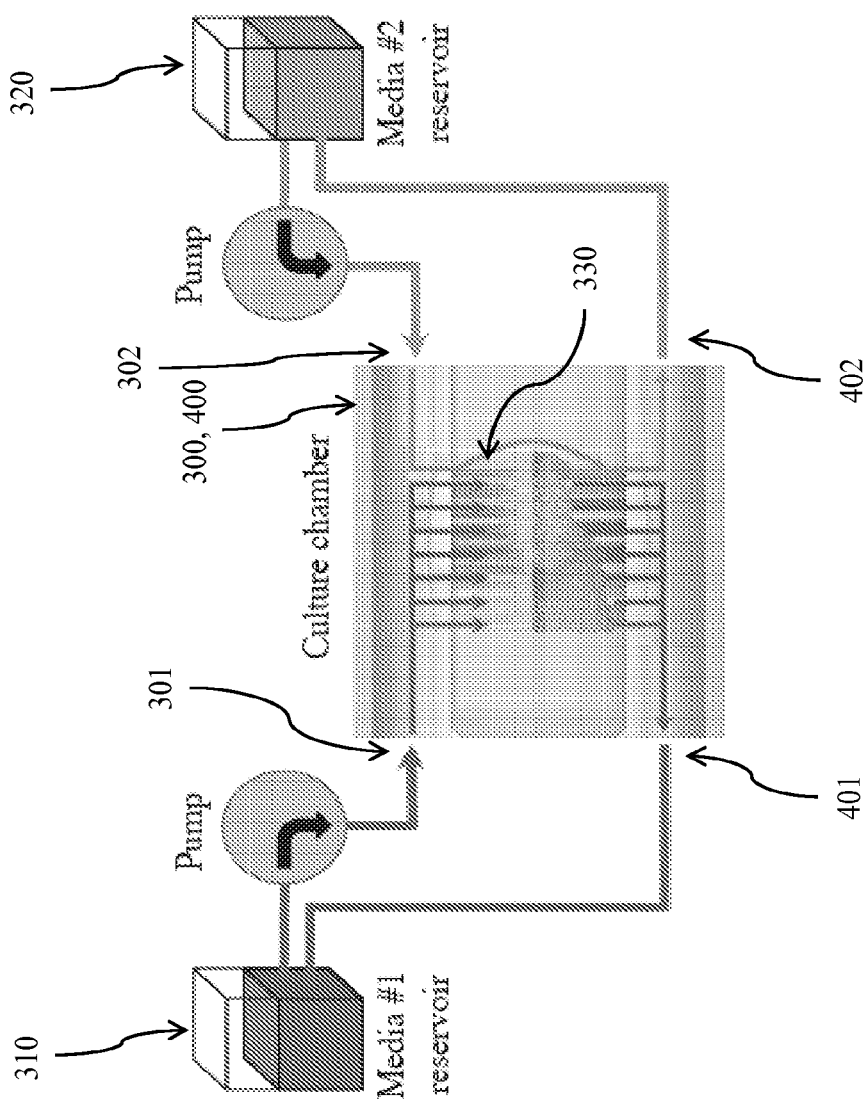
FIG. 3 is a schematic view of an exemplary embodiment of dual medium perfusion in accordance with the disclosed subject matter.

FIG. 3 demonstrates the fluid-routing manifolds 300, 400 with two inlets 301, 302 and two outlets 401, 402 (wherein the direction of flow is denoted by the arrows) allowing introduction of two different types of fluid 310, 320 ("Media #1" and "Media #2"). The fluid-routing manifolds 300, 400 spatially distribute flowing fluid into different regions of the PDMS block 200 and to the scaffold 100.

Large constructs require a well-controlled nutrient supply to support cell viability and stimulate tissue formation. For control medium perfusion, channels 330 within the PDMS block 200 are sized according to the local scaffold thickness and are positioned to provide a desired fluid flow scheme throughout the scaffold.

Figure 4A:
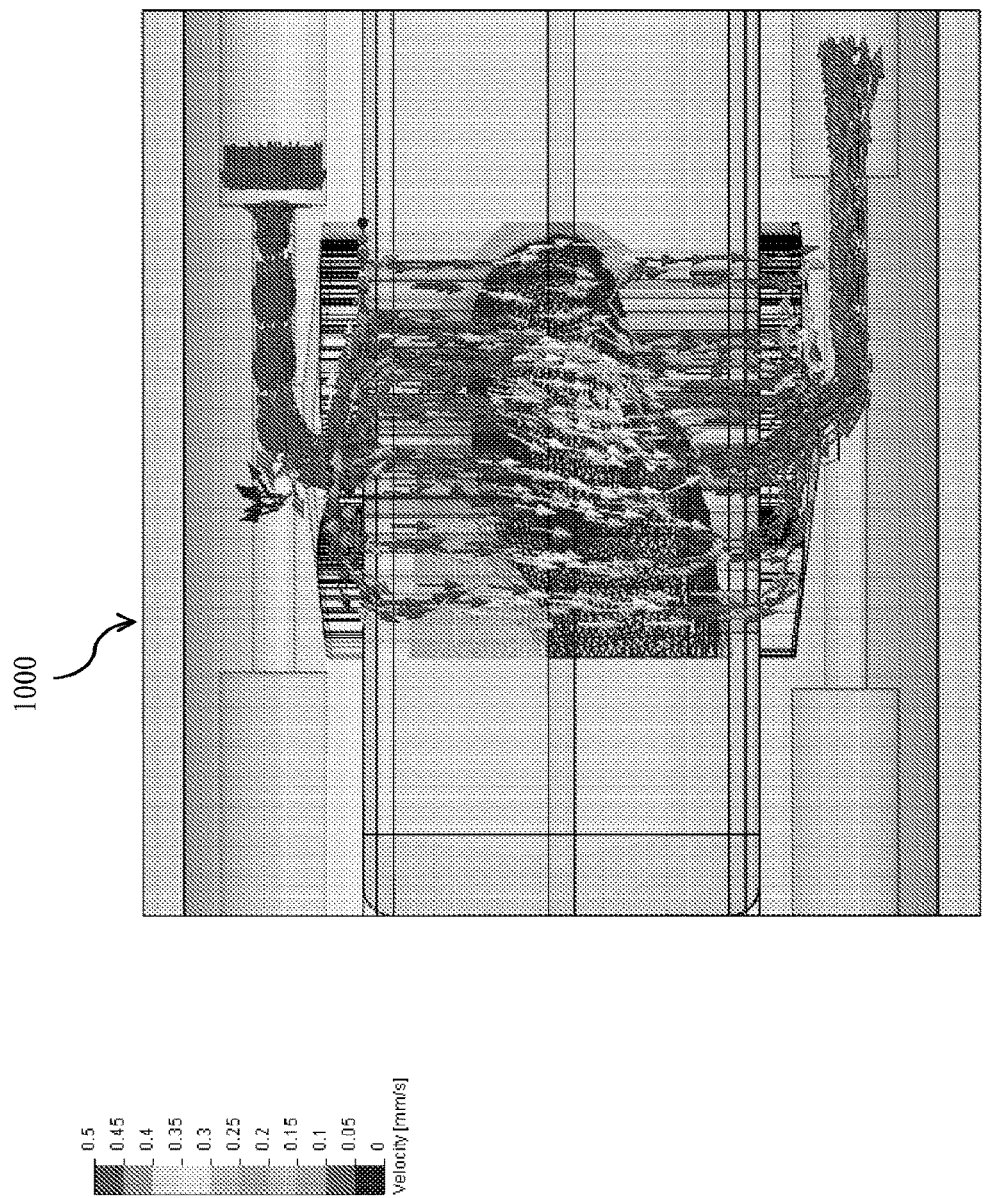
FIGS. 4A-B are computational fluid dynamic plots demonstrating flow simulation, which can determine desired fluid flow scheme and design PDMS block.
Figure 4B:
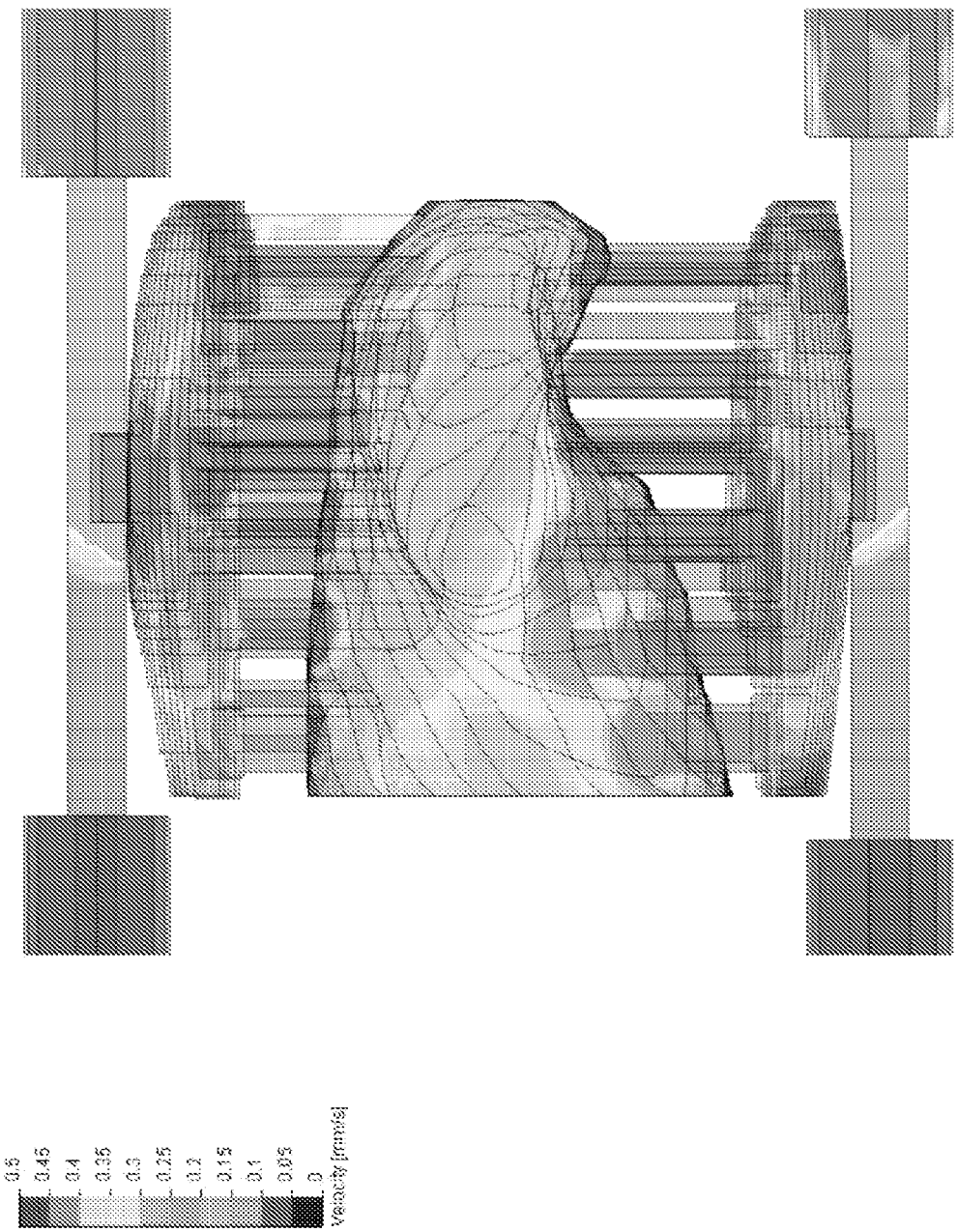

FIG. 4 depicts flow simulation for a given design as predicted using computational fluid dynamics data calculation and visualization techniques. For example, in order to obtain close-to homogenous fluid flow velocity in anatomically shaped scaffolds that have different thicknesses in different locations, the larger-diameter channels can be placed in the thicker region and smaller diameter channels are placed in the thinner region, in a way providing the exact same flow path resistance. Additionally or alternatively, the spacing of the channels in either region can be defined (e.g., for a specific type and density of cells) to provide a desired substantial concentration, i.e., oxygen in the tissue space.

Figure 5:
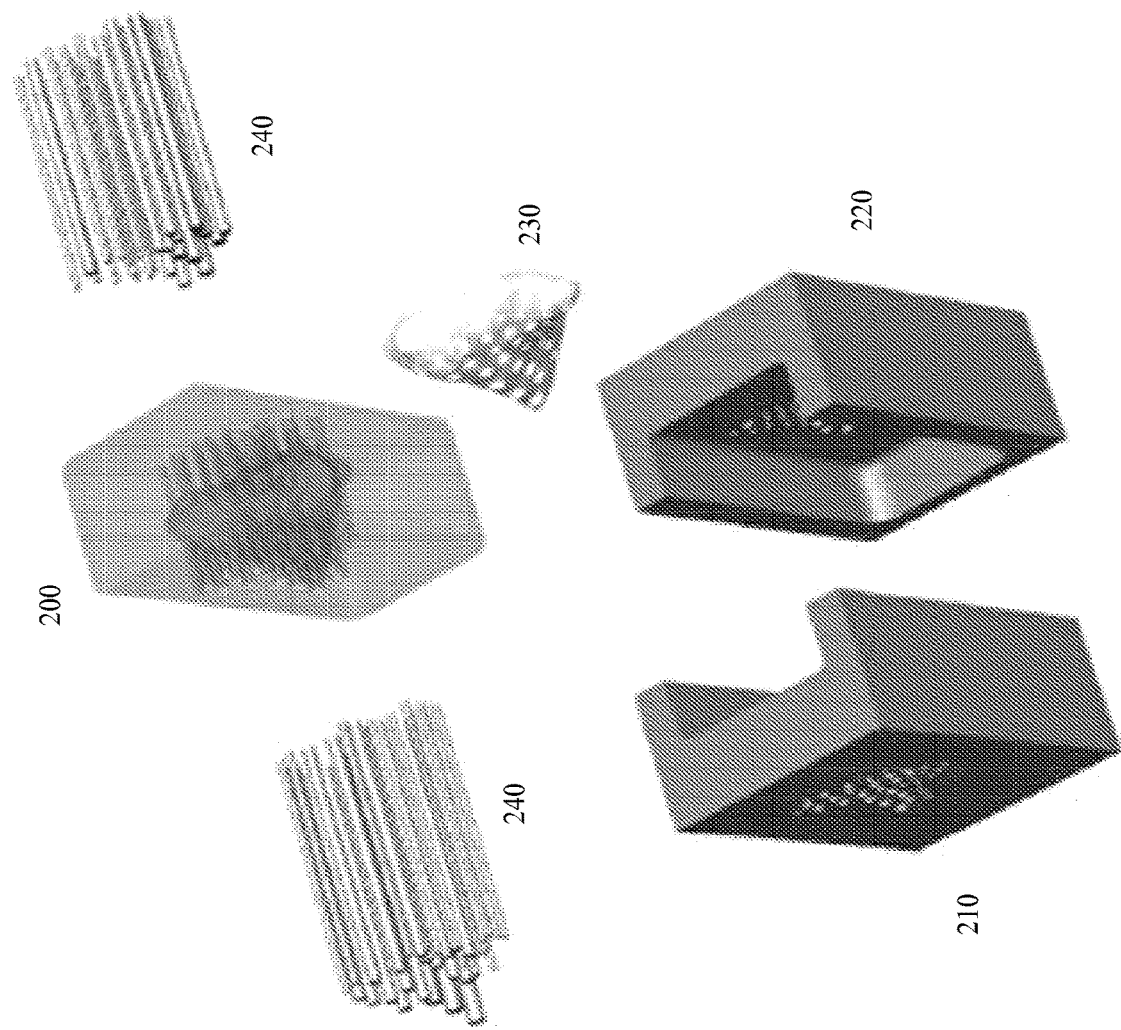
FIG. 5 is a schematic representation of an exploded-view of an exemplary PDMS block fabrication technique in accordance with the disclosed subject matter.

The number, sizes and placement of perfusion channels can be determined by computational flow dynamics modeling to obtain desired distribution scheme of fluid flow. Once the distribution and size of channels to provide desired scheme of fluid flow is determined for a given embodiment, the mold to create PDMS block can be created, as shown in FIG. 5. In the exemplary embodiment shown, the PDMS block fabrication technique includes four components: two cases with predetermined channels 210, 220; a positive scaffold-shape mold with predetermined channels 230; and rods 240 of various sizes. The mold is used to create a PDMS block 200.

Figure 6:
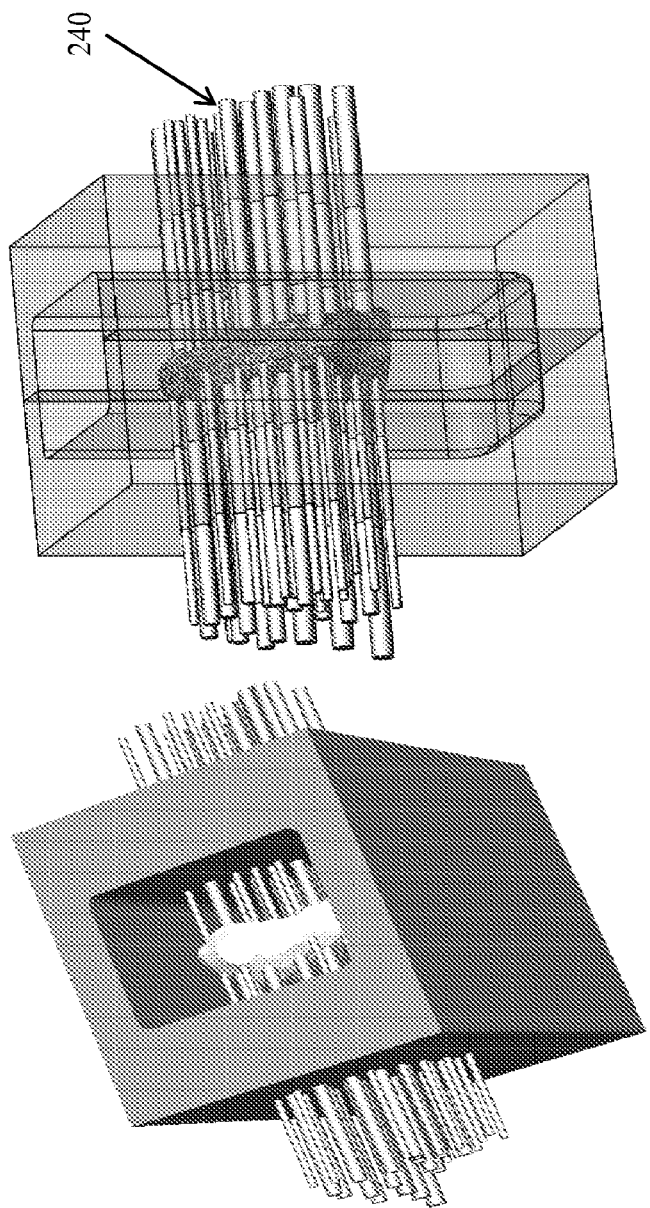
FIG. 6 is a schematic representation of the assembled PDMS block fabrication of FIG. 5.

The positive scaffold-shape mold and the outside casing containing the pre-determined holes for channels can be fabricated via 3D printed or machined. Multiple rods 240 are inserted through the pre-determined holes of the outside casing 210, 220 into the positive scaffold-shape mold as shown in FIG. 6. PDMS is poured into the empty space between the two casings and cured to create the negative PDMS block with pre-determined channels. The rods are then removed to create channels with various size and locations, the PDMS block is cut and the positive scaffold-shape mold is removed.

In accordance with another aspect of the disclosure, and for purpose of illustration and not limitation, the materials used to assemble this bioreactor are silicone and plastics, such as polycarbonate and polyetherimides (e.g., Ultem), to allow for monitoring compatibility in CT or MRI. The whole chamber can be place in the imaging machines without having to remove or open any parts allowing for sterility during imaging.

Figure 7:
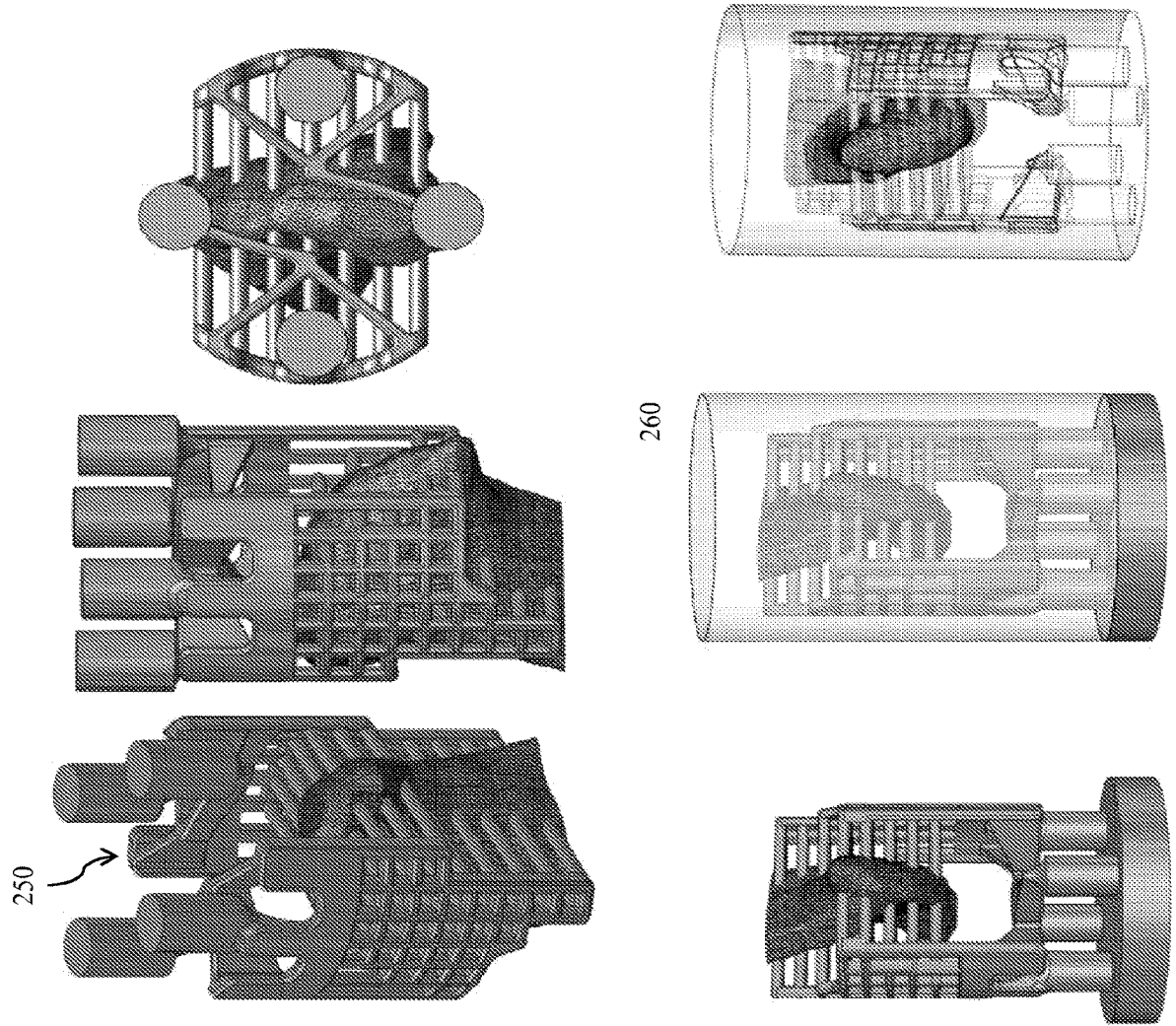
FIG. 7 is a schematic representation of an exploded-view of another exemplary PDMS block fabrication technique in accordance with the disclosed subject matter.

An additional method to fabricate the PDMS block is accomplished via casting PDMS over a 3D printed structure of the manifold channels in a low-melting-temperature material (e.g., wax) as shown in FIG. 7. Here, wax or dissolvable material is 3-D printed to create positive mold 250. The mold is inserted into a case 260 and PDMS can be poured from the top. Once cured, the temperature is raised to purge the wax from the PDMS, resulting in a PDMS manifold. This same process could also be accomplished with a dissolvable material (e.g. water-soluble).

In accordance with the present disclosure, the system and methods disclosed herein provide various advantages. The present disclosure enables the design of the fluid-routing manifolds that control spatial distribution of one or more types of culture medium into the PDMS block. A PDMS block may have multiple channels of different sizes and spacing at any desired location. The block is designed by computational flow simulation to match a desired fluid flow distribution within the scaffold. Methods to fabricate the channeled PDMS block are provided. The design of the bioreactor is compatible with real-time imaging (e.g., by µCT and MRI). Various alternative methods to fabricate the channeled PDMS block(s) are provided.

Figure 8:
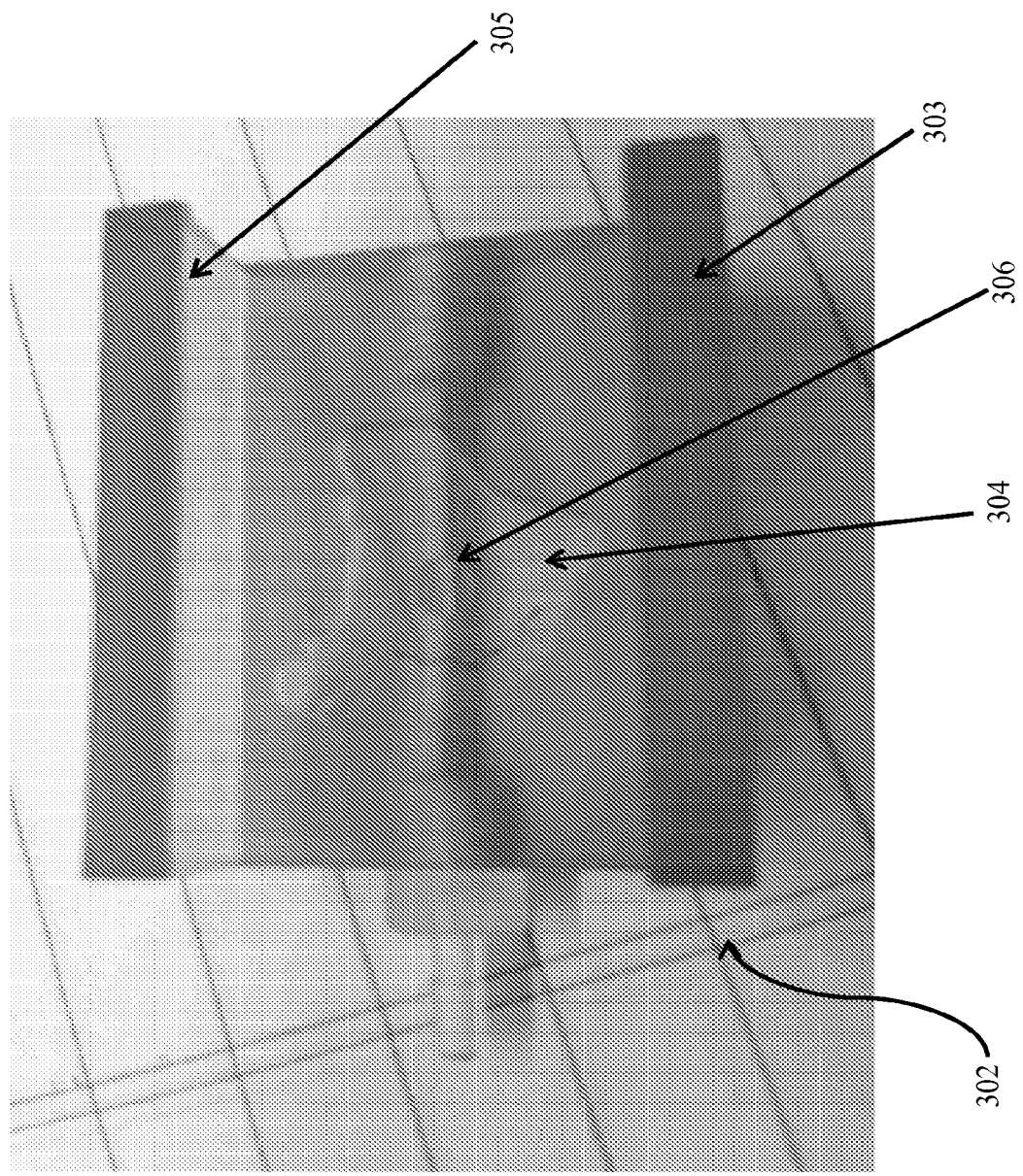
FIG. 8 is a schematic view of an alternative embodiment of a manifold, in accordance with the disclosed subject matter.
Figure 9:
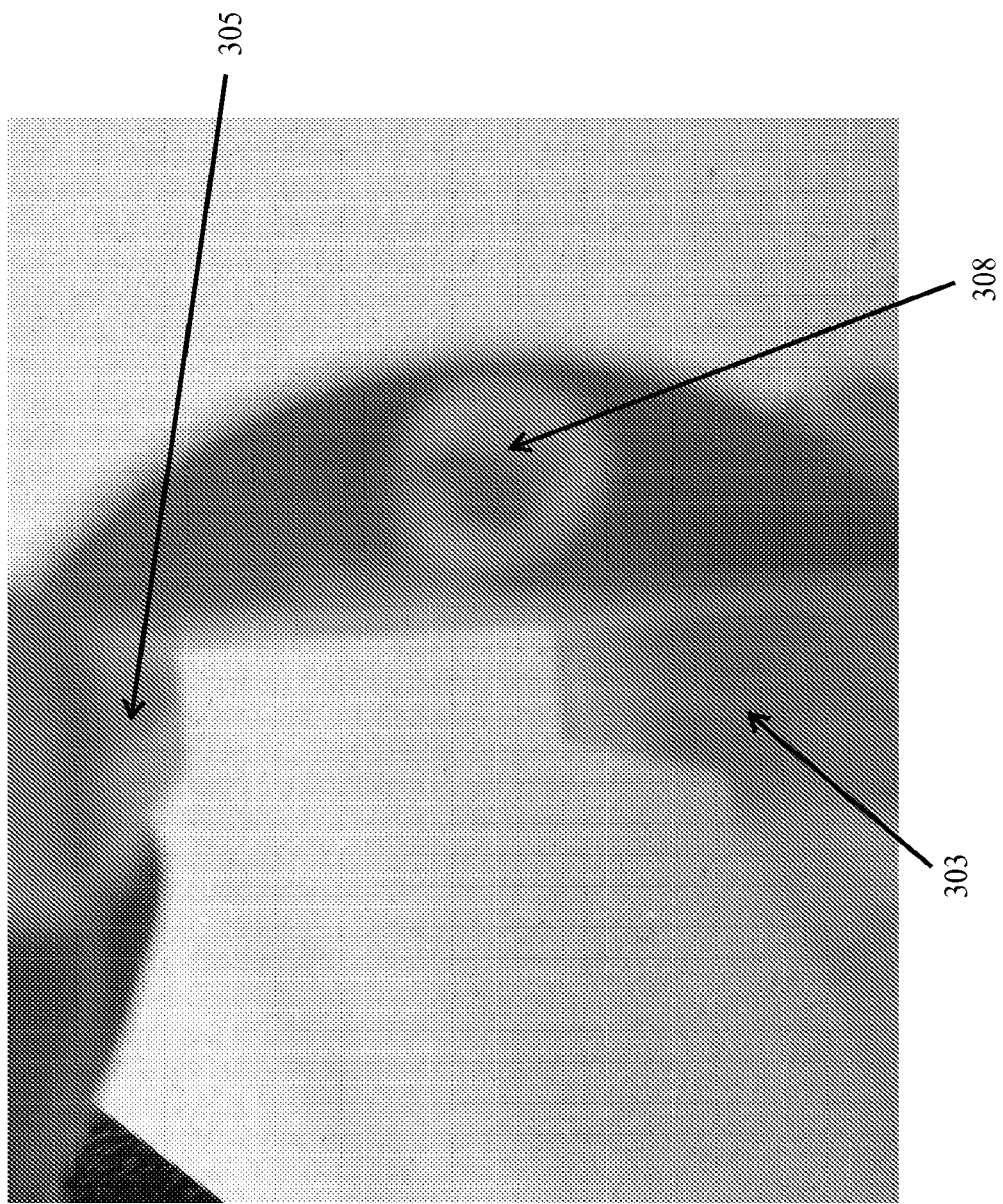
FIG. 9 is a front view of the embodiment of FIG. 8.

Additional exemplary embodiments of the disclosed subject matter are provided in FIGS. 8-13. As shown in FIGS. 8-9, the manifold 302 can be configured with generally planar inner surfaces which include an upper and lower flange that extends radially inward when in the assembled position (or out of the page as shown in FIG. 8). The manifold 302 also includes a recess portion 304 disposed on a planar side extending between the upper and lower flanges. The recess portion 304 is sized and shaped to accommodate a similarly shaped scaffold and/or tissue growth. Furthermore, port 306 is positioned within the recess portion 304 and is configured to allow fluid transfer in a direction that is orthogonal to the longitudinal axis of the bioreactor, when in the assembled position. Fluid is supplied and/or removed from the inner surfaces of the manifold 302 via port 308, as shown in FIG. 9.

Figure 10:
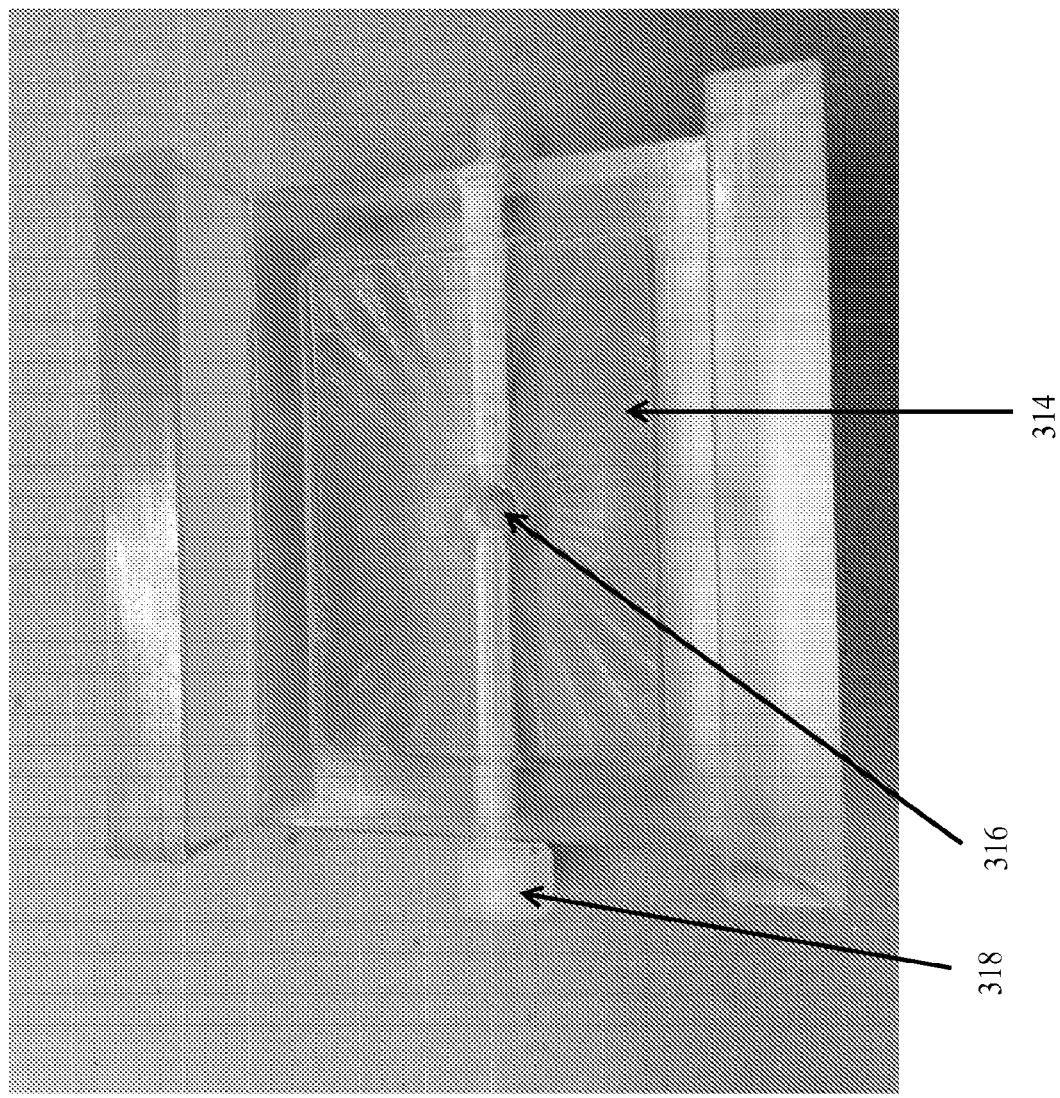
FIG. 10 is a schematic view of an alternative embodiment of a manifold, in accordance with the disclosed subject matter.

Similarly, FIG. 10 depicts another embodiment of the manifold 312. In this embodiment the recess portion 314 is configured with a rectangular shape and includes a plurality of channels extending radially outward from the port 316. As described above with respect to the embodiment of FIG. 9, fluid is supplied and/or removed from the inner surfaces of the manifold 312 via port 318.

Figure 11:
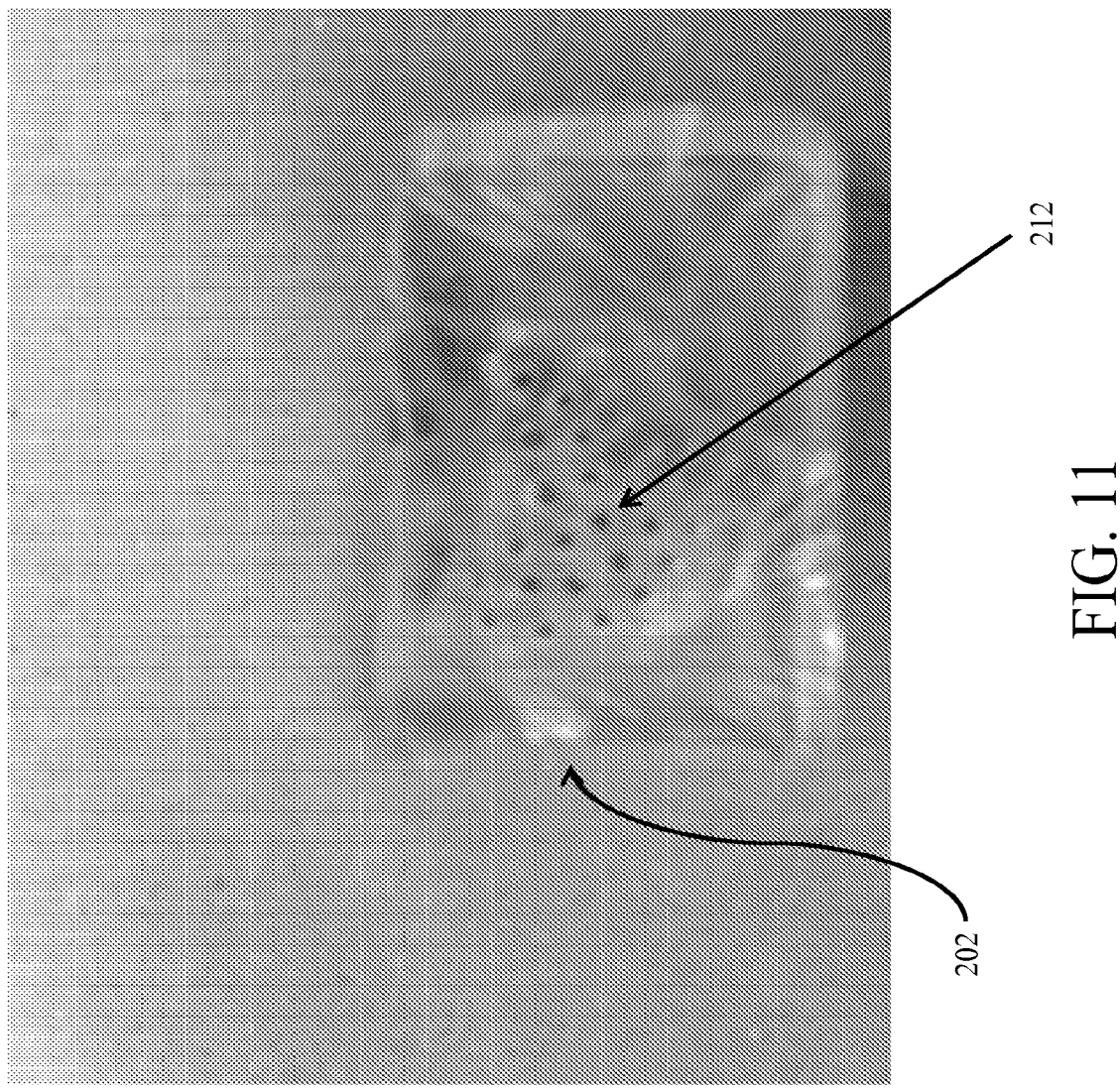
FIG. 11 is an alternative embodiment of the PDMS block, in accordance with the disclosed subject matter.

FIG. 11 depicts an exemplary PDMS block 202 having a plurality of holes or pores 212 disposed there out to facilitate fluid transfer and tissue generation. The sizes of the holes can vary along any given dimension of the scaffold. Likewise the concentration or density of the holes can very along any given dimension of the scaffold.

Figure 12:
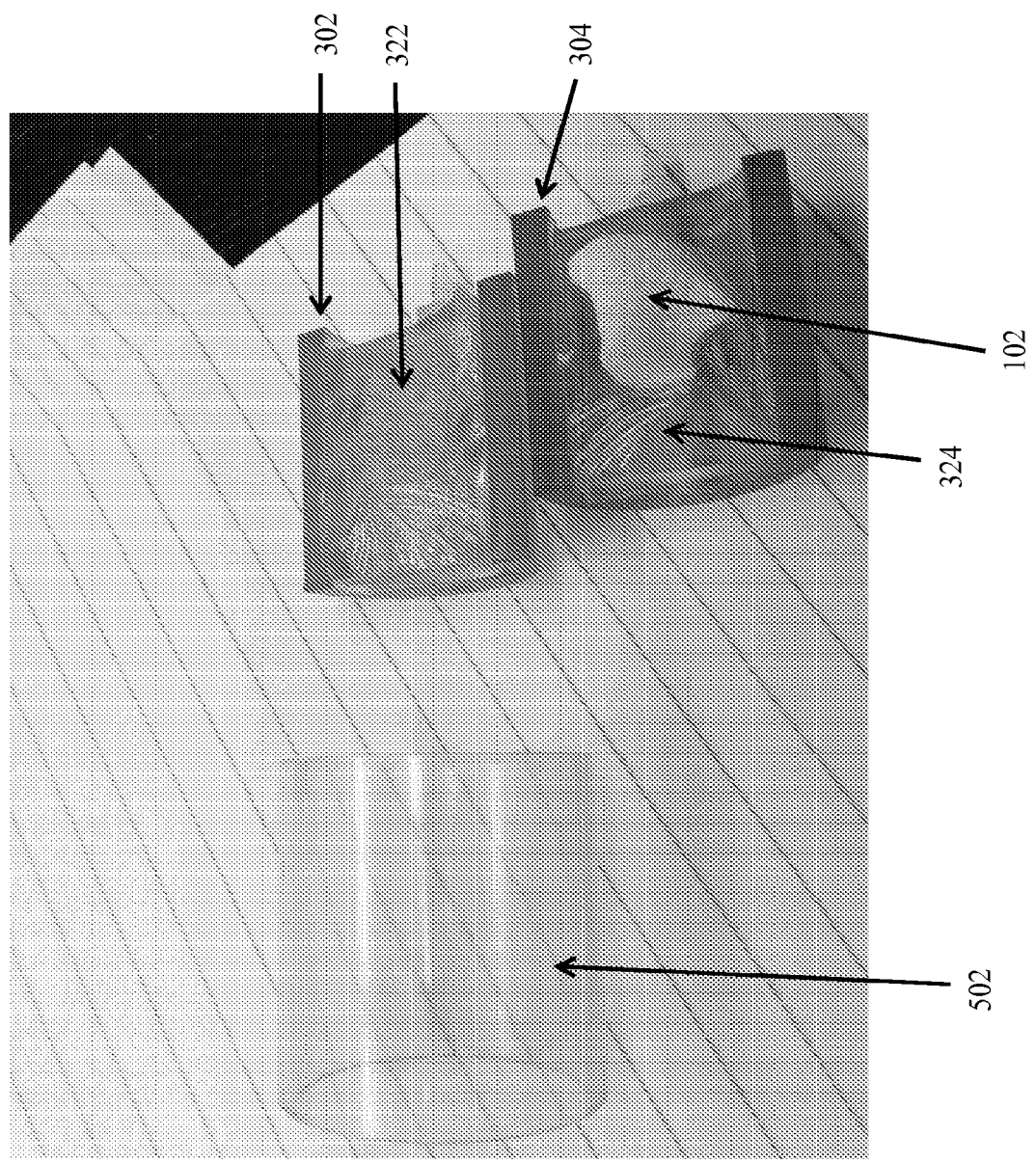
FIG. 12 is a schematic representation of an exploded-view of the components of an alternative embodiment of the bioreactor culture chamber in accordance with the disclosed subject matter.

FIG. 12 depicts exemplary manifolds 302 and 304, which can be configured to receive fluid routing blocks 322 and 324. In the embodiment shown, fluid routing blocks 322 and 324 are configured as separate and discrete parts, which are inserted within the manifolds 302, 304. These fluid routing blocks 322 and 324 in turn are matingly and sealingly coupled to enclose a scaffold 102. Fluid routing blocks 322 and 324 can be configured with varying sizes, shapes, and concentration of channels to rout fluid, as so desired. When assembled, these components are nested and coupled and inserted within the case 502.

Various embodiments of the present disclosure are useful for transport and storage of native tissues, for example allografts for implantation. The harvest, evaluation and matching of allografts of bone and cartilage can take about a month (of which about two weeks is attributable to harvesting and screening and two weeks is attributable to tissue matching). During this time, cell viability decreases to the range of 15-50%. Devices according to the present disclosure maintain the viability of these grafts. For example, osteochondral allografts have limited availability and a short shelf life of only about 14 days. By placing an ostechondral allograft into a perfusion bioreactor according to the present disclosure, the tissue may be maintained and supported so as to extend the shelf life of the osteochondral tissue.

Figure 13:
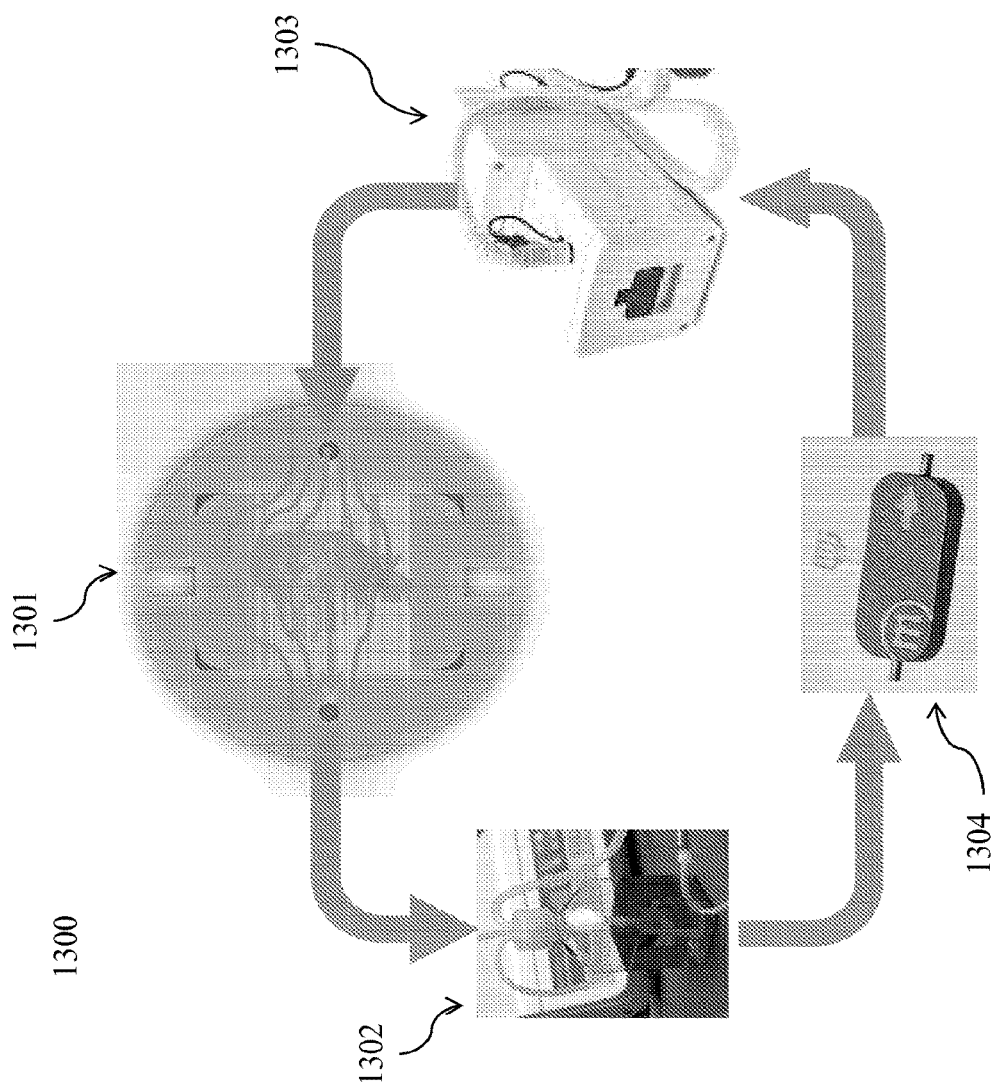
FIG. 13 is a diagram of a system for the maintenance of cell viability for osteochondral allografts according to an embodiment of the present disclosure.

Referring to FIG. 13, a system 1300 for graft maintenance is shown. A graft chamber 1301, such as describe further above, is coupled to an environmental control unit 1303 and a media reservoir 1302. Each is in fluid communication with micro-pump 1304. Micro-pump 1304 circulates the media through the environmental control unit 1303 and the graft chamber 1301. In some embodiments, micro-pump 1304 is battery powered.

While the disclosed subject matter is described herein in terms of certain preferred embodiments, those skilled in the art will recognize that various modifications and improvements may be made to the disclosed subject matter without departing from the scope thereof. Moreover, although individual features of one embodiment of the disclosed subject matter may be discussed herein or shown in the drawings of the one embodiment and not in other embodiments, it should be apparent that individual features of one embodiment may be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A method of making an anatomically-shaped bone graft comprising:
   preparing a complex scaffold to have a predetermined anatomical shape and placing the anatomically-shaped scaffold in a bioreactor, wherein the bioreactor comprises:
   at least one PDMS block comprising an internal chamber that matches the shape of the complex scaffold and a plurality of fluid routing channels of different sizes and spacing;
   a plurality of manifolds, wherein the plurality of manifolds are in communication with the plurality of fluid routing channels, wherein the at least one PDMS block is configured to be nested within the plurality of manifolds;
   wherein the plurality of fluid routing channels are sized and positioned with larger-diameter channels placed in relation to thicker regions of the complex scaffold and smaller-diameter channels placed in relation to thinner regions of the complex scaffold so that each of the plurality of fluid routing channels provides the same flow path resistance within the complex scaffold; and
   a case, the case disposed exterior of the complex scaffold, at least one PDMS block and plurality of manifolds;
   seeding the complex scaffold with stem cells;
   perfusing perfusate comprising nutrients through the complex scaffold for a period of time sufficient to enable the perfusate to permeate the complex scaffold and the cells to proliferate such that a viable bone graft is formed.

2. The method of claim 1, wherein the complex scaffold is seeded with human mesenchymal stem cells.

3. The method of claim 1, wherein the plurality of channels provides a desired concentration of oxygen in a tissue space throughout the complex scaffold.

4. The method of claim 1, wherein fluid flows through the complex scaffold at a velocity that provides a nutrient solution throughout the scaffold.

5. The method of claim 1, further comprising a process for transporting the bone graft in the bioreactor.

6. A method of making a tissue graft comprising:
   preparing a complex scaffold having different thickness in different regions and placing the complex scaffold in a bioreactor, wherein the bioreactor comprises:
   a block having at least one side, an approximately central cavity, wherein the complex scaffold is disposed within the approximately central cavity, and a plurality of channels extending from the at least one side to the approximately central cavity;
   a fluid routing manifold having an inlet and an outlet, the fluid routing manifold in fluid communication with the plurality of channels; wherein the plurality of channels are sized and positioned with larger-diameter channels placed in relation to thicker regions of the complex scaffold and smaller-diameter channels placed in relation to thinner regions of the complex scaffold so that each of the plurality of channels provides the same flow path resistance within the complex scaffold; and an enclosure disposed about an exterior of the fluid routing manifold;

seeding the complex scaffold with stem cells;

perfusing perfusate comprising nutrients through the complex scaffold for a period of time sufficient to enable the perfusate to permeate the complex scaffold and the cells to proliferate such that a viable tissue graft is formed.

7. The method of claim 6, wherein the complex scaffold is seeded with human mesenchymal stem cells.

8. The method of claim 6, wherein the plurality of channels provides a desired concentration of oxygen in a tissue space throughout the complex scaffold.

9. The method of claim 6, wherein fluid flows through the complex scaffold at a velocity that provides a nutrient solution throughout the complex scaffold.

10. The method of claim 6, further comprising a process for transporting the tissue graft in the bioreactor.

11. The method of claim 6, wherein the complex scaffold is anatomically shaped.

12. The method of claim 6, wherein the tissue graft is a bone graft.

\* \* \* \* \*